| United States Patent [19] | [11] Patent Number: 4,631,148 |
| Braksmayer et al. | [45] Date of Patent: Dec. 23, 1986 |

[54] FLAME RETARDANT ALLYLIC ESTERS OF TETRABROMOPHTHALIC ACID AND FLAME RETARDANT POLYMERS CONTAINING SAME

[75] Inventors: Diza P. Braksmayer, Cranbury; Fui-Tseng H. Lee, Princeton; Fred R. Scholer, East Windsor, all of N.J.

[73] Assignee: FMC Corporation, Philadelphia, Pa.

[21] Appl. No.: 712,060

[22] Filed: Mar. 15, 1985

[51] Int. Cl.$^4$ .................. C09K 21/00; C07C 69/76; C07C 69/80

[52] U.S. Cl. ........................... 252/609; 560/83

[58] Field of Search .................. 560/83; 252/609

[56] References Cited

U.S. PATENT DOCUMENTS 4,405,761  9/1983  Rodgers et al. ............... 560/83 X
4,543,418  9/1984  Rodgers et al. ............... 260/83 X Primary Examiner—John F. Terapane
Assistant Examiner—S. Wolffe
Attorney, Agent, or Firm—R. D. Jackson; E. G. Horsky; E. G. Seems

[57] ABSTRACT

1-allyl-2-hydroxyalkyl-3,4,5,6-tetrabromophthalates and flame retardant thermosetting polyester compositions containing them are described.

6 Claims, No Drawings

FLAME RETARDANT ALLYLIC ESTERS OF TETRABROMOPHTHALIC ACID AND FLAME RETARDANT POLYMERS CONTAINING SAME

This invention relates to flame retardant polymer compositions. More particularly, the invention is concerned with flame retardant thermosetting polymer systems in which the flame retardant agency therefor is an allylic ester derivative of tetrabromophthalic acid.

Flame retardant polymer compositions, formed by the copolymerization of an ethylenically unsaturated component and diallyl tetrabromophthalate as a flame retardant, are known chemical entities. In preparing these compositions, the unsaturated component typically comprises a mixture of an ethylenically unsaturated copolymerizable monomer and a vinylic unsaturated thermosetting polymer, commonly an unsaturated polyester. Illustrative of the latter are the polyester condensates of a dihydric alcohol with a dicarboxylic acid containing vinylic unsaturation. These unsaturated polyester resins are particularly useful when glass fibers are dispersed therein as reinforcement. Pipes, panels and the like can be formed from such reinforced thermosetting resins.

The diallyl tetrabromophthalate copolymerizes with the unsaturated component(s) in the polymerizable mixture and thereby becomes part of the polymer substrate and cannot be displaced therefrom. Such is not the case with simple additive fire retardants which are subject to leaching and/or vaporization if plastic articles are exposed to solvents or elevated temperatures.

Although diallyl tetrabromophthalate is a highly effective fire retardant, its solubility and/or compatibility in unsaturated polyester systems is not as high as might be desired. This can make it difficult to produce thermosetting plastics containing high levels of diallyl tetrabromophthalate.

It has now been discovered that certain new and novel allylic tetrabromophthalates afford improved solubility in thermosetting resin formulations and the provision of said allylic tetrabromophthalates and unsaturated polyester polymers containing them constitutes the principal object and purpose of the invention.

The allylic tetrabromophthalates of the invention can be represented by the following general formula:

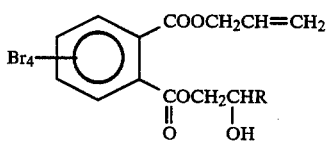

wherein R is hydrogen or aliphatic, such as an alkyl group, generally in the range of 1 to about 10 carbon atoms, for example, methyl, ethyl, n-propyl, sec-butyl, hexyl, octyl, etc. Preparation of the compounds is effected in accordance with the reaction scheme depicted below.

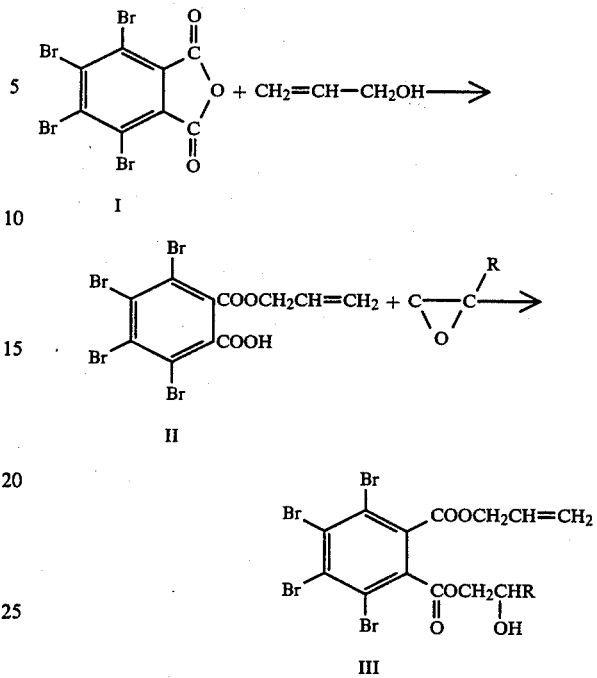

In carrying out the reactions aforesaid, intermediate compound II is formed by heating tetrabromophthalic anhydride with excess allyl alcohol in an inert, normally liquid organic solvent in the presence of a base such as a tertiary organic amine, for example, triethyl amine. Convenient solvents are the aromatic hydrocarbons as exemplified by toluene or xylene. Reaction temperatures are typically in the neighborhood of about 100° C. to about 150° C. After the reaction is complete, the ethylene oxide component is introduced into the reactor to convert compound II into final product. In conducting the second-stage reaction, the reactor is sealed to maintain elevated pressures; temperatures are in the range of about 100° C. to about 150° C. The contents of the reactor are washed with water, then sodium bicarbonate and then again with water. After concentrating in vacuo to remove solvent and volatiles, compound III is recovered as a viscous liquid.

The allylic tetrabromophthalates herein will copolymerize with the typical polyesters, for example, polyesters which are polyester condensates of a polybasic acid and a glycol and having sufficient unsaturation whereby it will thermoset when appropriately catalyzed with a vinyl polymerization catalyst. The criteria for such products are well established in the art. For the most part, about 25 to 50 mol percent of the polybasic acid is unsaturated of which maleic acid is an example; the glycol is difunctional. These condensates are mixed with an unsaturated copolymerizable monomer such as styrene, methyl acrylate, methyl methacrylate and the like.

In formulating the flame retardant polymers of the invention, the allylic tetrabromophthalate flame retardant herein will constitute by weight from about 10% to about 50% of the total polymerizable material. At these concentrations, not only do the polymers exhibit excellent fire retardancy but they also possess good mechanical properties. In other words, at loads sufficient to attain flame retardancy, the allylic tetrabromophthalates of the invention do not significantly lower heat deflection temperature or cause an undue drop in flexural strength.

The flame retardancy of the polymers was tested and evaluated as measured by UL-94. In this procedure, flammability is designated as follows:

| UL-94: | |
|---|---|
| Sample Size | 5 inch × 0.5 inch × 1/16 inch. |
| Sample Placement | Clamped at top to hang vertically so that bottom end is 12 inches above a dry cotton swatch. |
| Flame | ⅜ inch bunsen burner blue flame. |
| Monitor | Place flame centrally at lower end of sample for 10 seconds. Remove and record time to self-extinguish. Immediately place burner at end of sample for another 10 seconds; remove and record time to self-extinguish. Repeat above for five samples. |
| Ratings | |
| V-0 | Sample burn <10 seconds after either flame exposure. Total burning <50 seconds for all five samples (10 exposures). No samples with glowing up to clamp. No dripping samples that ignite cotton. No samples with glowing <30 seconds. |
| V-1 | Samples burn <30 seconds after either flame exposure. Total burning <250 seconds for all five samples (10 exposures). No samples with glowing up to clamp. No dripping samples that ignite cotton. No samples with glowing >60 seconds. |
| V-2 | Samples burn <30 seconds after either flame exposure. Total burning <250 seconds for all five samples (10 exposures). No samples with glowing up to clamp. Samples drip flaming particles which burn, only briefly, some of cotton. No samples with glowing >60 seconds. |

Oxygen index was determined by ASTM Method D2863-74; an oxygen index of about 27–28 or higher is generally considered acceptable. Other tests carried out on the flame retardant polymers of the invention include such well-known physical measurements as flexural strength, flexural modulus, Barcol hardness and heat distortion temperature (HDT).

Reference is now made to the following nonlimiting examples which illustrate the invention more specifically.

EXAMPLE 1

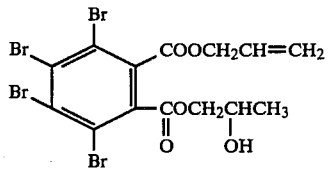

1-Allyl-2-Hydroxypropyl-3,4,5,6-Tetrabromophthalate

Into a one liter stainless steel reactor equipped with stirrer, pressure gauge, heater and liquid addition pump, was placed tetrabromophthalic anhydride (280 g, 0.6 m), allyl alcohol (53 g, 0.9 m), triethylamine (1.1 g, 0.01 m), and toluene as solvent (250 ml). The reactor was sealed and heated to 125° C. and maintained at that temperature for 40 minutes. Propylene oxide (72 g, 1.24 m) was slowly pumped into the reactor as the reactor temperature was maintained at 125° C. Gauge pressure was noted at 15 psig. There was little pressure change during the oxide addition. After oxide addition was complete, heating at 125° C. continued for one hour. The reactor was then cooled to room temperature and an amber clear liquid was isolated. This was washed with water, saturated aqueous sodium bicarbonate, and water again. The organic layer was concentrated under reduced pressure to 325 g of a syrupy clear dark amber liquid.

Elemental Analysis: Calculated: C 28.97; H 2.07; Br 55.17; Found: C 29.26; H 2.08; Br 54.33

Proton NMR indicated a monoallyl monopropylated product. Mass spectroscopy (via chemical ionization) showed a parent ion peak (581) and fragment peaks.

EXAMPLE 2

Isophthalate Polyester Composition and Flame Retardant Polymer Produced Therefrom The monoallyl monopropylated diester of tetrabromophthalic acid of Example 1 was formulated in Aropol ® 7240 isophthalic/maleic unsaturated polyester resin (Ashland Chemical Co.) and room temperature cured using 6% cobalt naphthenate (1 phr) as a promoter, mercaptobenzothiazole (0.5 phr) as an accelerator, and t-butylperbenzoate (2 phr) as the catalyst. Laminates were constructed as follows: 2 ply of 1.5 oz. chopped strand type E glass mat, 1 ply 10 mil type C glass surfacing veil on each side. Clear castings were prepared using resin or resin and bromine source but no filler. A control containing no bromine was prepared for comparison. The control was cured using 6% cobalt naphthenate (0.5 phr) as a promoter and methylethyl ketone peroxide (1.25 phr) as the catalyst. All cured products were post-cured at 100° C. for two hours. Both control and bromine-containing laminates were formulated with antimony trioxide (5 phr).

The results of testing the flame retardant polymers of Example 2 aforesaid are itemized in Table I below.

TABLE I

| 1-Allyl-2-Hydroxypropyl-3,4,5,6-Tetrabromophthalate In Unsaturated Isophthalic Polyester | | |
|---|---|---|
| | Isophthalic Control Resin | Isophthalic Resin/ Tetrabromophthalate |
| Flexural Strength (psi) | 23460 | 19590 |
| Flexural Modulus (psi) | 8.93 × 10$^5$ | 8.71 × 10$^5$ |
| Barcol Hardness | 57 | 54 |
| UL-94 (1/16 inch) | Burns | V-O |
| Oxygen Index | 21.0 | 29.4 |
| HDT (°C.) | 94 | 78 |
| % Bromine | 0 | 9.45 |

As is clearly evident from an inspection of the data in Table I, polymers from thermosetting polyesters containing the 1-allyl-2-hydroxyalkyl-3,4,5,6-tetrabromophthalate of the invention exhibit excellent flame retardancy and good mechanical properties.

What is claimed is:

1. A compound of the formula:

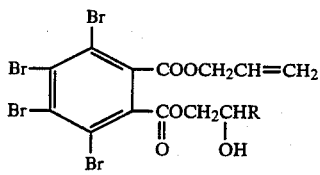

wherein R is an aliphatic group of 1 to 10 carbon atoms.

2. A compound according to claim 1 wherein R is methyl.

3. A flame retardant thermosetting composition comprising a copolymer of an ethylenically unsaturated component capable of further polymerization to the thermoset stage with an allylic flame retardant compound of the formula:

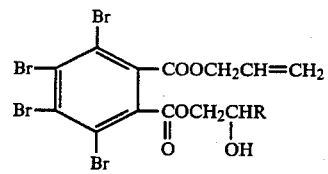

wherein R is an aliphatic group of 1 to 10 carbon atoms.

4. The composition according to claim 3 wherein R in the formula is methyl.

5. The composition according to claim 3 wherein the ethylenically unsaturated component is a polyester of a glycol and a polybasic carboxylic acid.

6. The composition according to claim 5 wherein 25 to 50 mol percent of the polyester is unsaturated.

* * * * *